United States Patent [19]

Le Corre et al.

[11] 4,230,624
[45] Oct. 28, 1980

[54] PROCESS FOR THE SYNTHESIS OF DERIVATIVES OF THE BENZOFURAN, CHROMENE AND ISOCHROMENE TYPE

[75] Inventors: Maurice Le Corre, Rennes; Alain Hercouet, Betton; Béatrice Bégasse, Rennes, all of France

[73] Assignee: Agence Nationale de Valorisation de la Recherche, Neuilly S. Sein, France

[21] Appl. No.: 938,653

[22] Filed: Aug. 31, 1978

[30] Foreign Application Priority Data

Sep. 2, 1977 [FR] France .................... 77 26686
Aug. 16, 1978 [FR] France .................... 78 23894

[51] Int. Cl.² .................... C07D 311/02; C07D 307/79
[52] U.S. Cl. .................... 260/345.2; 260/346.22; 260/346.71; 568/11; 568/14
[58] Field of Search ............ 260/345.2, 346.22, 346.71

[56] References Cited
PUBLICATIONS

Bieber et al., J. of Organic Chem., vol. 27 (1962), pp. 678–679.

*Primary Examiner*—Henry R. Jiles
*Assistant Examiner*—Bernard Dentz
*Attorney, Agent, or Firm*—Schwartz, Jeffery, Schwaab, Mack, Blumenthal & Koch

[57] ABSTRACT

The invention relates to a process for the production of therapeutic compounds of the benzofuran, chromene and isochromene type of the general formula;

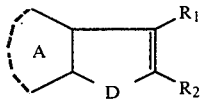

in which formula,

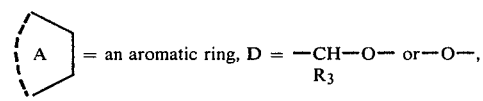

$R_1$ and $R_3 = H$, lower alkyl, aralkyl or cycloalkyl
$R_2 = H$ or an organic radical
and when
$D =$

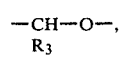

$R_1$ and $R_3$ may represent an organic radical.

The process comprising the cyclization in the liquid phase and in the presence of a base a compound of the formula;

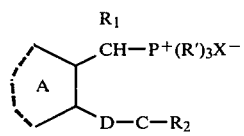

in which formula;
$R' =$ an alkyl, aryl or aralkyl radical and
$X^- =$ an anion.

21 Claims, No Drawings

PROCESS FOR THE SYNTHESIS OF DERIVATIVES OF THE BENZOFURAN, CHROMENE AND ISOCHROMENE TYPE

The present invention relates to a process for synthesising derivatives of benzofuran, chromene and isochromene type.

The present invention has for its object to provide a new process which permits a general synthesis of derivatives of benzofuran, chromene and isochromene type, which is much flexible and more profitable than the existing processes.

This process, which can be used more particularly for synthesising benzofuran derivatives, is of considerable importance, taking into account the fact that:

(a) the benzofuran derivatives are pharmacologically active products which are of extreme interest;

(b) no general synthesis of benzofuran derivatives exists;

(c) the existing synthesis procedures lead to small yields; and that (d) certain benzofuran derivatives are at the present time unavailable by the known synthesis procedures.

Among the numerous articles which relate to the physiological activity of benzofuran derivatives, a recent statement (R. Royer, Actualités de chimie thérapeutique, 3rd Series, 1975) reveals the considerable importance of benzofuran derivatives in spheres such as:

cardiovascular field: vasodilators, spasmolytics,
microbiology: anti-bacterial agents
parasitology
nervous system: stimulants, tranquillisers
endocrinic system
herbicides
phytohormones
photosensitisers.

The last Index Nominum includes 16 compounds (medicaments and pigmentation agents) which have the benzofuran structure.

As regards the procedures for synthesising benzofuran derivatives, two statements on this subject have been recently published, one of which is a very general statement concerning all the benzofuran derivatives (P. Cagnant and D. Cagnant, Advances in Heterocyclic chemistry, Vol. 18, 1975, Academic Press, New York), while the other is limited to the 2-alkyl- and 2-aryl-benzofurans (A. Areschka and coll. S. A. Labaz, Industries chimiques Belges 1972, 37, page 89).

It becomes apparent from this last article that: none of the very large number of methods of obtaining them has a truly general character, the preparation of certain compounds of great importance still remains difficult; for example, 2-isopropyl benzofuran is only obtained with a yield of 40% in the best of the examples.

As regards the synthesis of compounds of isochromene type, the position is even more difficult, because at the present time only three synthesis processes are known; a synthesis with the aid of isochrominones, (C. Normant-Chefnay, Bull. Soc. chim. Fr., 2, 1351 (1971), the synthesis using isocoumarines (.J. N. Chatterjea, Ber., 91, 2636 (1958) and the synthesis using 1-cyanobenzocyclobutene (R. Hug, H. J. Hansen, H. Schmid, Helv. chim. Acta, 55, 10, (1972). The yields of these processes rarely exceed 10% and the possibilities of the synthesis thereof are limited.

As for the synthesis of chrom-3-enes, essentially three processes for the preparation thereof are available, which use either a Claisen transposition of propargyl ether, followed by a cyclisation (Zsindely and H. Schmid, Helv. chim. Acta, 51, 1510 (1968), or chroman-4-ones (F. Baranton, G. Fontaine and P. Maitte, Bull. Soc. chim. Fr, 4203 (1968), or chromanes, by dehydrogenation in the presence of quinone (D. Walker and J. D. Hiebert, Chem. Rev., 67, 153 (1967).

It is also necessary to mention a synthesis of chrom-3-enes which, in common with the process of the invention, makes use of a phosphonium salt. It is a question of the Schweizer synthesis (E. E. Schweizer et coll., J. Org. Chem., 38, No. 8, 1583 (1973), which utilises the condensation in DMF or HMPT of a sodium salt of salicyl aldehyde with vinyl phosphonium salts.

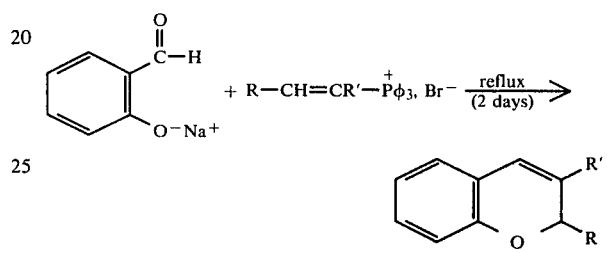

However, this operating procedure has the disadvantage of using vinyl phosphonium salts which, with the exception of a few of them, are not readily available.

None of these synthesis procedures is sufficiently flexible for permitting chrom-3-enes to be prepared at will.

The present invention is concerned with a process for preparing oxygenated heterocyclic compounds of formula I:

in which

represents a cycle of aromatic character, D represents a radical

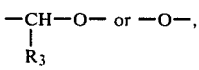

$R_1$ and $R_3$ representing a hydrogen atom or a lower alkyl, aryl, aralkyl or cycloalkyl radical and, when D represents a radical

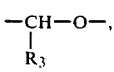

$R_1$ and $R_3$ may represent an organic radical, and $R_2$ represents H or an organic radical, characterised in that a compound of formula II:

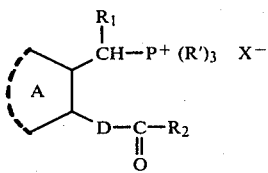   (II)

in which R' represents an alkyl, aryl or aralkyl radical and $X^-$ is an anion, is cyclised in the presence of a base in liquid phase.

In the foregoing formulae, the cycle of aromatic character

will generally be benzene, but it is possible to visualise other aromatic cycles having 5 or 6 linkages and comprising one or more hetero atoms, such as pyrrol, furan, thiophene and the diazines such as pyrazine.

The cycle of aromatic character could, in addition, be formed by several condensed cycles, provided that the cycle linked to the oxygenated cycle in formula I is one of aromatic nature, for example, naphthalene, quinoxaline or chromene.

The cycle of aromatic nature may be substituted once or several times in any arbitrary manner, particularly by an oxo, nitro or hydroxy function or by one or more halogens or by an organic radical.

The organic radicals, which may be substituents of

or are indicated in the meaning of $R_1$ and $R_3$, are particularly the $R_{10}$ radical, which is an alkyl, alkenyl, alkynyl, aryl, aralkyl, aralkenyl, aralkynyl or cycloaliphatic radical, or even an

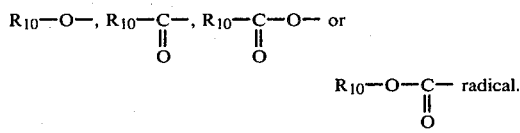

The $R_2$ radical will preferably be the $R_{10}$ or $R_{10}$—O— radical and particularly the radical of a carboxylic acid of formula

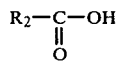

or of a halogenated ketone of formula

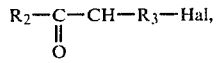

in which Hal is a halogen.

Among the alkyl radicals, it is particularly necessary to mention the straight-chain or branched-chain lower alkyl radicals, having from 1 to 8 carbon atoms, such as methyl, ethyl, propyl, i-propyl, butyl and n-octyl.

Among the alkenyl radicals, it is particularly necessary to mention the radicals having an ethylenic unsaturation or having conjugated double bonds and capable of having up to 20 carbon atoms.

Among the alkynyl radicals, it is necessary to mention particularly the radicals having from 1 to 7 carbon atoms, such as the acetylenyl or propargyl radicals.

The aryl radicals are preferably the phenyl radical, or phenyl substituted by one or more alkyl, alkoxy or nitro radicals, or the heteroaryl radicals, such as furanyl or pyridyl.

The cycloaliphatic radicals are particularly the cycloalkyl radicals, for example the $C_3$ to $C_7$ radicals, such as cyclopropyl or cyclohexyl.

The other radicals which have been mentioned are derived without any difficulty from the foregoing, as well as the aralkyl radicals preferably comprising the previously mentioned aryl radicals in the aryl portion and the previously mentioned alkyl radicals in the alkyl portion.

$X^-$ is an anion, preferably the $Br^-$ anion.

Among the compounds of formula II which are of particular interest, it is necessary to mention the compounds of formula

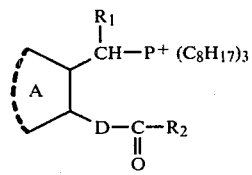  IIα and

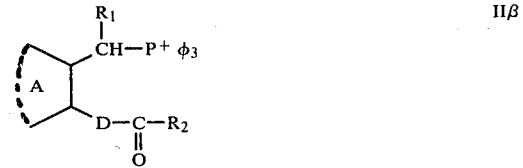  IIβ this being particularly because the cyclisation of the compound of formula IIα leads to the formation of the compound of formula I, but also to the formation of the trioctylphosphine oxide of formula

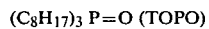

which is a valuable product, since it is used in the liquid-liquid extraction of uranium from natural phosphates, the uranyl nitrate forming a complex with the TOPO;

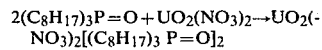

The compound of formula IIβ is also of interest, because it may be prepared from triphenyl phosphine, which is an inexpensive product.

The base which is used in the cyclising operation according to the present invention is a base which is adequate for deprotonising the carbon in the α position of the phosphonium grouping so as to form an intermediate phosphorane of formula:

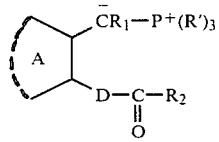

Among the bases capable of being used, it is necessary to mention the alcoholates and the hydroxides of alkali metals, such as sodium t-amylate or potassium t-butylate and caustic soda or caustic potash.

The liquid medium being used may form a homogeneous or heterogeneous phase.

Thus, when toluene is used, the operation is carried out in heterogeneous phase, but when using chlorinated solvents, this operation takes place in homogeneous phase.

It is also possible to operate in the presence of two liquid phases by a phase transfer mechanism, for example, a mixture of water and $CH_2Cl_2$.

The liquids which are preferred for carrying out the process according to the invention are mainly the non-polar aprotic solvents, such as the aromatic solvents: benzene, toluene; the halogenated hydrocarbons: chloroform, dichlorethane; and the ethers: ethyl ether or propyl ether, or tetrahydrofuran.

It is likewise possible to employ the polar protic solvents, particularly water, or the polar aprotic solvents, such as DMSO, HMPT, but these latter are of less interest on an industrial basis, in view of the cost thereof.

It is obvious that the preceding liquid phase, even when it is homogeneous, may be formed by a mixture of the preceding solvents.

No other very critical parameters exist in respect of the reaction, which preferably develops with reflux of the reaction mixture and at normal pressure, except in the case of phase transfer, when the reaction develops at ambient temperature and pressure.

Nevertheless, when the reaction mechanism being used is of the phase transfer type, it will be possible to employ a phase transfer catalyst, such as a quaternary ammonium salt, for example $Bu_4N$ $I^-$, $Et_3C_6H_5CH_2NCl^-$ or a phosphonium salt.

The evolution of the reaction may be easily followed, because the intermediate phosphorane which is formed is generally coloured. Hence, by dropwise addition of the base to the liquid containing the phosphonium salt, the coloration of the phosphorane is seen to appear and then disappear.

The cyclisation essentially leads to the desired product and to the phosphine oxide which, taking into account the very large difference in the solubility thereof, are separated without any difficulty.

It is thus possible to extract the compound I by means of petroleum ether or pentane, in which $(R')_3PO$ is insoluble, or it is even possible to extract $(R')_3PO$ with ethanol, in which it has good solubility.

It is obviously possible to visualise other types of separation which are known in the chemical field, when this is necessary.

Thus, when a trioctylphosphonium derivative is used, the trioctylphosphine oxide (TOPO) is obtained, which can be separated by distillation from the reaction mixture, washing with water and filtration of the distillation residue.

In the operational procedure of the process according to the present invention, the following are prepared when starting with:

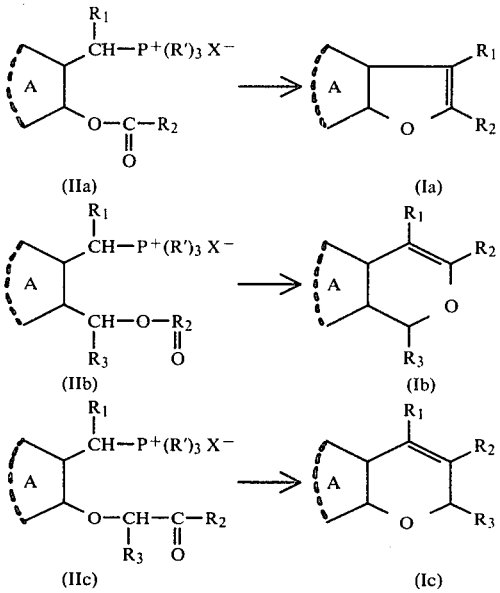

that is to say, derivatives of benzofuran type (Ia), isochromene type (Ib) or of chrom-3-ene type (Ic), when

represents benzene.

Obviously involved in this case are main basic skeletons, which may be synthesised by the process according to the present invention, but it is possible to include them in more complex cyclic systems, for example, compounds of furo(2,3-g)coumarine type of structure:

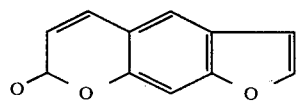

such as psoralene, methoxysalene or trioxysalene, which are photosensitisers, or compounds of furochromone type, of structure:

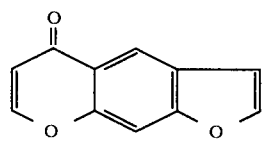

such as khellinone, which are vasodilators, or derivatives of furonaphthazine type of structure:

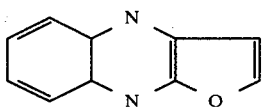

The phosphonium salt of formula IIa which can be used when carrying out the process according to the invention may be simply prepared and with very good yields by the following reaction:

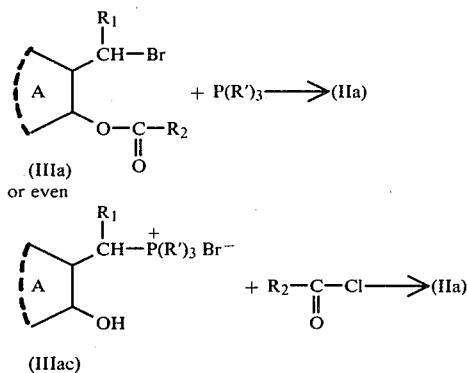

The choice of the reaction is essentially dependent on the nature of the substituent $R_2$. Actually, the preparation of the compound IIIa generally implies a bromation, but the latter cannot be carried out if $R_2$ is sensitive to bromation, particularly if it contains a bond of ethylenic character. This substituent will then be fixed at the end of the reaction sequence, starting from IIIac.

The reaction of the brominated derivative IIIa with phosphine is practically quantitative, by operating in the presence of two reagents in equimolar quantity, under heat or at ambient temperature, in a solvent such as toluene, or without solvent. The reaction takes several hours, but may be developed at ambient temperature and then requires several days. The phosphonium salt crystallises in the form of fine crystals without any initiation or priming.

It is preferably triphenylphosphine which is employed as phosphine $P(R')_3$, because it is readily available and easy to employ, whereas the other phosphines, especially the trialkylphosphines, are very expensive and very toxic. Nevertheless, it is necessary to find a separate position for the trioctylphosphine (TOP), because the use of this phosphine leads to compounds of formula IIα and, by cyclisation, the trioctylphosphine oxide (TOPO) is obtained which, as has already been previously stated, is a compound of very great interest in the extraction of uranium. The obtaining of this valuable by-product permits a very appreciable reduction in the cost of the process for synthesising the compounds of formula I.

In addition, the use of TOP makes it possible to operate in organic solutions which are more concentrated than triphenylphosphine, and this makes it possible to visualise the reduction in the size of the reactors or the increase in the productivity thereof.

The esterification of the hydroxyl compound IIIac is preferably carried out with the aid of acid chloride or anhydride in a solvent, such as chloroform, in the presence of a fixation agent of the hydrogen chloride, such as pyridine.

The phosphonium salt IIb may be prepared by carboalkoxylation of the brominated derivative of formula:

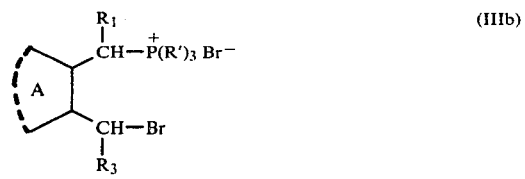

by a carboxylate of formula:

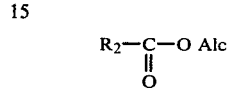

in which Alc represents an alkali metal.

The reaction is carried out, for example, with the reflux of a hydroacetonic solution of the corresponding sodium carboxylate and of the compound IIIb.

The phosphonium salt of formula IIc may either be obtained as the compound IIa, by action of the phosphine on the brominated derivative of formula IIIc:

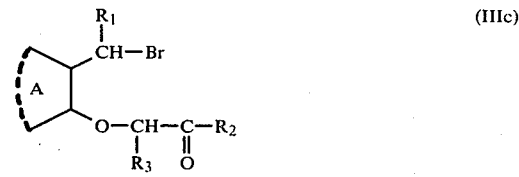

but, although this method is capable of being used, and taking into account the danger of a secondary bromation reaction of the carbonylated chain at the time of the action of the bromine, when the compound IIIc is prepared, it is preferable to pass by way of the oxaphospholene of formula:

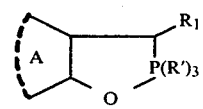

on which is caused to react a halogenated ketone of formula:

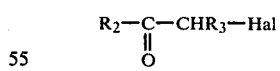

in an equimolar quantity in solution in a solvent, such as dichloromethane, benzene, toluene or ethyl ether.

The oxaphospholene is prepared in situ without any isolation, starting from the compound of formula IIIac, by action of a base such as t-AmONa, t-BuOK, NaH, $NaNH_2$, in a solvent, such as benzene, toluene, ethyl ether or $CH_2Cl_2$. It is preferred to use the same solvent as in the preparation of IIIc.

The compound of formula IIIac is prepared by hydrolysis of the corresponding ester, which is generally the acetate, of formula IVac:

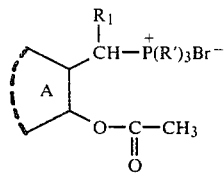
(IVac)

which is itself obtained by the action of phosphine on the brominated derivative of formula Vac:

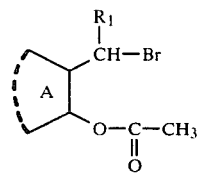
(Vac)

under conditions similar to those of the reaction of IIIa→IIa.

The compound of formula Vac is prepared by bromation of the compound of formula VIac:

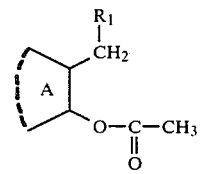
(VIac)

by action of an excess of bromine on the ester with ultraviolet irradiation, in a solvent such as $CCl_4$ or benzene.

The compound of formula VIac is prepared by esterifying the corresponding alcohol in known manner.

The compound of formula IIIa is obtained by bromation of the compound of formula IVa:

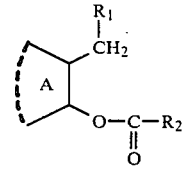
(IVa)

under the same conditions as described in respect of compound VIac.

This compound IVa is prepared by esterifying the corresponding alcohol in known manner.

The compound of formula IIIc is prepared by bromation of the compound of formula IVc:

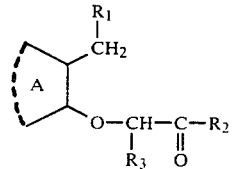
(IVc)

as in the preparation of the compound of formula Vac.

This compound IVc is prepared by etherifying the corresponding alcohol.

The compound of formula IIIb is prepared from the corresponding dibrominated derivative of formula:

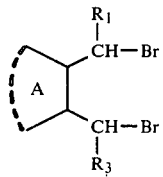

by the action of phosphine, as previously described. The use of a slightly polar solvent, such as toluene, in which the phosphonium salts are generally insoluble, enables a double quaternisation to be avoided.

The initial products used in the process according to the invention are known and can be prepared by known processes.

Thus, the compounds of formula

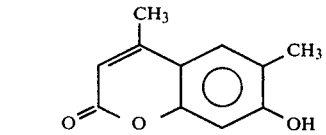

which are useful in the synthesis of furo[2,3-g]coumarines, can be obtained by a Pechmann condensation, for example, by the action of ethyl acetyl acetate on 2,4-dihydroxytoluene in the presence of a Friedel-Crafts catalyst.

Likewise, by the action of ethyl acetylacetate on 2,6-dihydroxytoluene, a compound is obtained corresponding to the formula

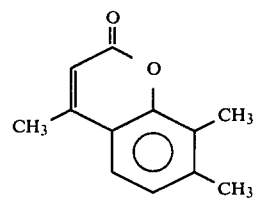

which gives access to the derivatives of angelicine.

Given below are two general diagrams concerned with the preparation of the derivatives according to the invention, in which

is the benzene ring, $R_1 = R_3 = H$ and $R' = \phi$.

The present invention permits the preparation of the effective active principles, especially in the pharmaceutical industry, such as 2-(p-nitrophenyl)-benzofuran, which is an anti-bacterial agent (P. K. Smarma, K. Mehta, O. P. Gupta, M. M. Mahavar and S. K. Mukerjii, J. Pharm. Sci. 1967, 56, 1007), the pterofurans and its derivatives, which are anti-hemolytic agents or active principles in connection with phytochemistry, such as euparine, and its derivatives, which are insecticides, in addition to the previously mentioned compounds, such as psoralenes and furochromones.

The compounds according to the present invention may also serve as an intermediary in the known synthesis processes of compounds such as benzarone, benzbromarone and benziodarone, starting from 2-ethyl benzofuran, of amiodarone, starting from 2-butyl benzofuran or of inicarone, starting from 2-isopropyl benzofuran.

The present invention is also concerned with a process for the preparation of trioctyl phosphine oxide, or TOPO, from trioctylphosphine, TOP, using the processes as described, in which $R' = C_8H_{17}-$.

The present invention is also concerned with the products which are obtained by employing the processes as described.

DIAGRAM I

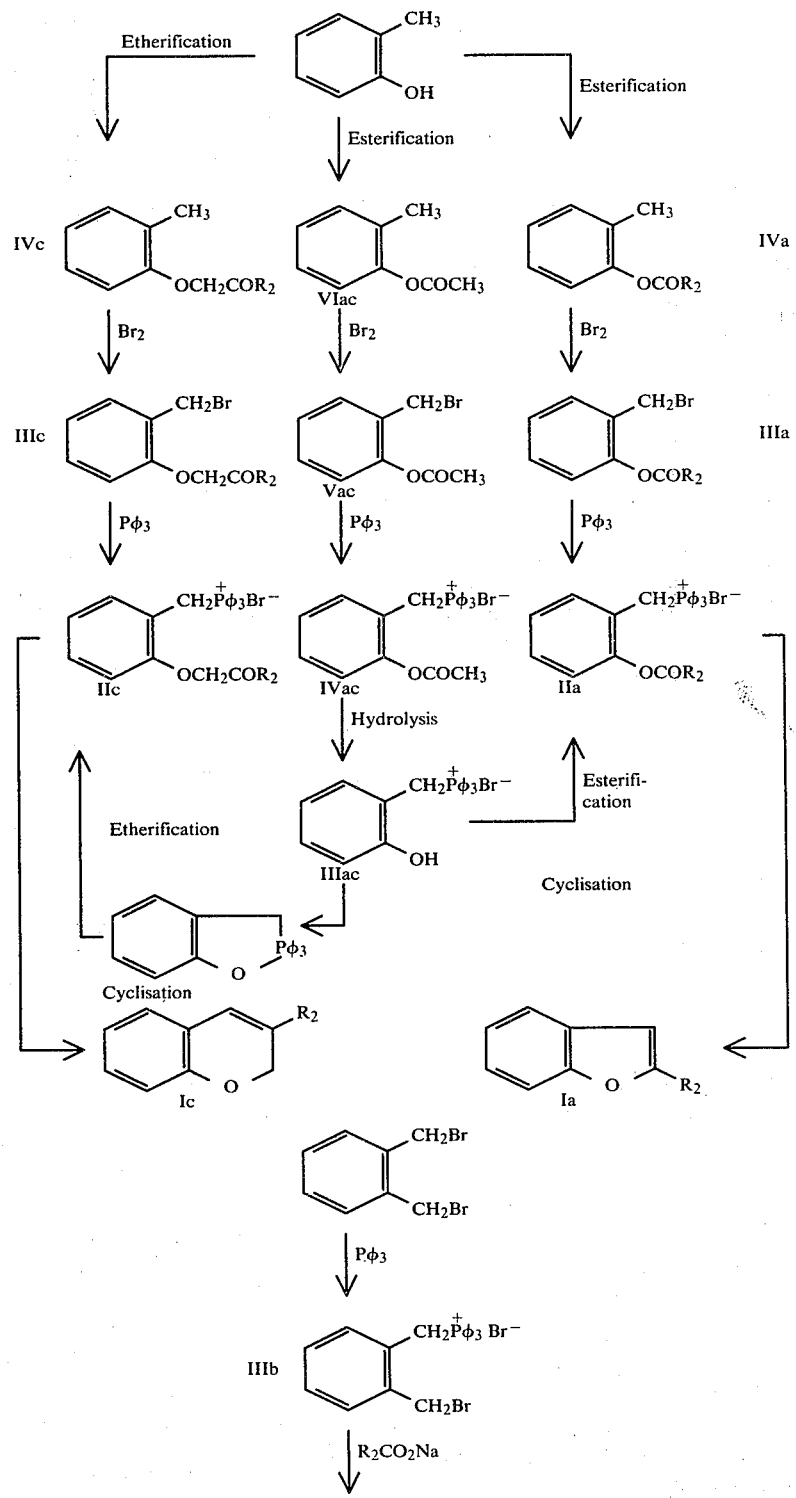

-continued
DIAGRAM I

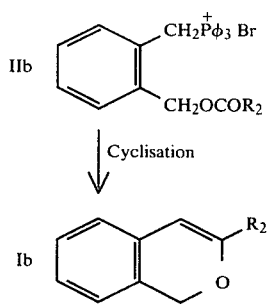

DIAGRAM II

The following examples are intended to illustrate the exploitation of the process according to the present invention:

EXAMPLE 1

Preparation of 2-ethyl benzofuran (A) Esterification of o-cresol

Into a spherical flask equipped with a condenser, a dropping funnel and containing 2 mols of o-cresol are introduced, in 15 minutes, 2.2 mols of propionyl chloride. The mixture as obtained is heated at 110° C. for about 2 hours, until the discharge of hydrochloric acid ceases. The o-cresol propionate which is obtained is distilled under vacuum:

B.p.$_{15}$ = 114° C.; yield 98%.

(B) Bromation of o-cresol propionate

To a solution of 0.1 mol of o-cresol propionate in 150 cc of CCl$_4$ are added, with ultraviolet irradiation, in small fractions, and in proportion with the decoloration, 0.22 mol of bromine in 30 cc of CCl$_4$, the solvent is removed and the residue is distilled under reduced pressure. The 1-propionoxy-2-bromomethylbenzene is obtained:

B.p.$_{0.8}$ = 99° C.; yield 65%.

(C) Quaternisation of the bromide as obtained

A solution of 0.2 mol of 1-propionoxy-2-bromomethylbenzene and 0.2 mol of triphenyl phosphine in 200 cc of dry toluene is refluxed for 3 hours. After filtration on sintered glass, the phosphonium salt as obtained is dried under vacuum. The phosphonium salt of formula:

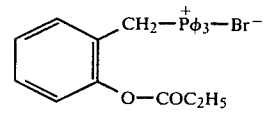

is obtained with a yield of 95%.

(D) Cyclisation

To a thoroughly stirred suspension of 0.05 mole of the preceding phosphonium salt in 150 cc of toluene under reflux are added dropwise in approximately 15 minutes and under a nitrogen atmosphere, 0.055 mole of an approximately normal solution of sodium t-amylate in toluene.

After filtration of the sodium bromide on a folded filter, the toluenic solution is evaporated and the residue is extracted with 200 cc of pentane.

After having been in a refrigerator for one night, so as to precipitate the last traces of φ$_3$PO, the ethyl benzofuran is isolated by evaporation of the pentane. Yield 95%.

EXAMPLE 2

Preparation of 2-butyl-benzofuran

By operating in accordance with Example 1, but by replacing the propionyl chloride by the chloride of valeric acid in stage (A), the o-cresol valerate is obtained:

B.p.$_1$ = 105° C.; yield 94%.

The bromide of stage (B) is obtained with a yield of 68%;

B.p.$_{0.8}$ = 132° C.

The phosphonium salt of stage (C) is obtained with a yield of 92%.

In stage (D), the 2-butyl benzofuran is obtained with a yield of 94%.

EXAMPLES 3 TO 7

By operating in accordance with Example 1 and by replacing the propionyl chloride in stage (A) by the compound of formula:

$$R-\underset{\underset{O}{\|}}{C}-Cl$$

the compounds of Table I are prepared:

TABLE I

| N° example |  R | Solvent | NMR SPECTRUM ($\delta$ in ppm/ in TMS) | |
|---|---|---|---|---|
| | | | H$_A$ ($\delta$) | Other signals ($\delta$) |
| 1 | C$_2$H$_5$ | CDCl$_3$ | 6,31 | CH$_2$ at 2,78, CH$_3$ at 1,30 |
| 2 | C$_4$H$_9$ | CDCl$_3$ | 6,40 | CH$_2$ in α of the cycle at 2,75 |
| 3 | CH$_3$ | CCl$_4$ | 6,41 | CH$_3$ at 2,45 |
| 4 | C$_6$H$_5$ | CCl$_4$ | 7,00 | |
| 5 | p-NO$_2$—C$_6$H$_4$— | C$_6$D$_6$ | 6,60 | |
| 6 | p-CH$_3$—O—C$_6$H$_4$ | CDCl$_3$ | 6,95 | CH$_3$ at 3,86 |
| 7 | CH$_3$O—⟨⟩— CH$_3$O—⟨ | CDCl$_3$ | 6,87 | CH$_3$ at 3,9 and 4,0 |

EXAMPLE 8

Operating in accordance with Example 1, but by replacing, in stage (A), the 2.2 moles of propionyl chloride by 4.2 moles of benzoyl chloride and the o-cresol by 2,6-dihydroxy toluene, there is obtained the 2-phenyl-4-benzoyloxy benzofuran, of formula:

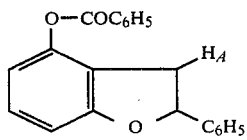

NMR (CDCl$_3$) $\delta H_A = 6.96$ ppm.

EXAMPLE 9

Operating in accordance with Example 1, but replacing, in stage (A), the propionyl chloride by acetyl chloride and the o-cresol by 3-methyl-4-hydroxy benzophenone, there is obtained the 2-methyl-5-benzoyl benzofuran of formula:

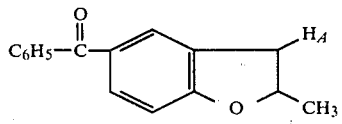

NMR (CDCl$_3$) $\delta H_A = 6.40$ and $\delta CH_3 = 2.4$.

EXAMPLE 10

Operating as in accordance with Example 9, but replacing, in stage (A), the 3-methyl-4-hydroxy benzophenone by phlorol, there is obtained the 2,3-dimethyl benzofuran:

NMR (CCl$_4$) $\delta CH_3 = 2.0$ and 2.2.

The foregoing examples make it possible directly to prepare the desired compound but, in certain cases, especially when the acid chloride being used has a double bond, the bromation of the stage (B) would lead to a bromation on the double bond, so that it becomes necessary to use a slightly longer process, in which the bromination is carried out prior to the acylation. The following examples illustrate this type of process.

EXAMPLE 11

Preparation of the 2-butyl benzofuran (A) Esterification of o-cresol

Into a spherical flask provided with a condenser, a dropping funnel and containing 2 moles of o-cresol, 2.4 moles of acetyl chloride are introduced in 15 minutes. The bath is kept at 110° C. until the release of hydrochloric acid is completed, i.e. after about 3 hours, and then the o-cresol acetate as obtained is distilled under vacuum:

B.p.$_{20}$ = 106° C.; yield 95%.

It must be observed that the reaction is exothermic and that the duration thereof is undoubtedly shorter than that as previously indicated. Nevertheless, it is essential to ensure the complete transformation of the cresol, because the presence thereof would be damaging in the bromination reaction.

(B) Bromination of o-cresol acetate

To a solution of 0.2 mole of o-cresol acetate (30 g) in 50 cc of dichloromethane are added, with ultraviolet irradiation and in small portions and in proportion to the decoloration, 0.22 mole of bromine (35.2 g) in 20 cc of dichloromethane. The solvent is eliminated and the 2-bromomethyl-1-acetyloxybenzene is distilled under reduced pressure.

B.p.$_2$ = 103°–105° C.; yield 77%.

(C) Preparation of the phosphonium salt

A solution of 45.8 g of the brominated derivative as previously obtained (0.2 mole) and of 52.4 g of triphenylphosphine (0.2 mole) in 200 cc of dry toluene is refluxed for 3 hours. After having been filtered on fritted glass, the phosphonium salt is dried in an oven at 103° C. for 5 hours. The compound of formula:

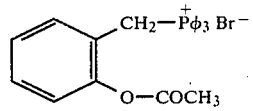

is obtained with a yield of 85%, the said compound showing a melting point of 223°–225° C.

(D) Hydrolysis of the phosphonium salt which is obtained

A suspension of 50 g of phosphonium salt as obtained in stage (C) is refluxed for 30 minutes in 500 cc of 5-normal hydrochloric acid. After adding 250 cc of water and 100 cc of CHCl$_3$, the chloroformic solution is decanted and the aqueous solution is extracted with 100 cc of chloroform. The phosphonium salt of formula:

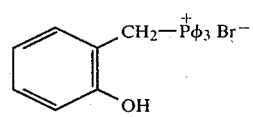

is obtained in anhydrous form and free from chloroform by azeotropic distillation of the chloroformic solution after treatment on sodium sulphate and by drying at a temperature of 150° C. for 1 hour.

(E) Esterification of the phosphonium salt

To a solution of 0.06 mole of phosphonium salt as previously obtained (24.24 g) in 50 cc of chloroform are added all at once 0.09 mole of valeric acid chloride and 0.12 mole of pyridine. After being refluxed for 2 hours, dilution is carriedut with 100 cc of chloroform, followed by washing with 40 cc of water and drying over sodium sulphate. By azeotropic distillation, using chloroform, followed by evaporation of the chloroform by means of a rotary evaporator, there is obtained the phosphonium salt of formula:

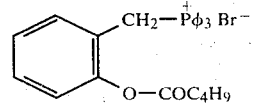

which is similar to the product of Example (2C), which crystallises by addition of 100 cc of ether; this salt is dried under vacuum at 110° C. for 3 hours.

(F) Cyclisation of the phosphonium salt

To a thoroughly agitated suspension of 0.05 mole of salt as previously obtained, in 150 cc of toluene, under reflux, are added dropwise in about 15 minutes and under a nitrogen atmosphere, 0.055 mole of a solution of normal sodium t-amylate in toluene.

After filtering the sodium salt on a folded filter, the toluenic solution is evaporated and the residue is extracted with 200 cc of pentane. After being left overnight in a refrigerator, so as to precipitate the last traces of $\phi_3PO$, the 2-butyl benzofuran is isolated by evaporation of the pentane.

EXAMPLES 12 TO 22

Operating as described in Example 11, but by replacement in stage (E) of the valeric acid chloride by the chloride of formula: R—CO—Cl, the compounds according to Table II are prepared:

TABLE II

| N° example | R | Solvent | $H_A$ (δ) | NMR SPECTRUM (δ in ppm/to TMS) Other signals (δ) |
|---|---|---|---|---|
| 12 | $C_2H_5$ | $CDCl_3$ | 6,31 | $CH_2$ at 2,78, $CH_3$ at 1,30 |
| 13 | $(CH_3)_2$—CH | $CDCl_3$ | 6,40 | Isopropyl CH at 3,05, $CH_3$ at 1,32 |
| 14 |  | $CDCl_3$ | 6,38 | Cyclopropanic CH at 1,93 |
| 15 | $C_4H_9$— | $CDCl_3$ | 6,40 | $CH_2$ in α of the cycle at 2.75 |
| 16 | $CH_3$—$(CH_2)_7$—CH=CH—$(CH_2)_7$— | $CDCl_3$ | 6,28 | Ethylenic protons at 5,33 |
| 17 | 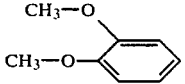 | $CDCl_3$ | 6,96 | |
| 18 | $C_6H_5$ | $CCl_4$ | 7,00 | |
| 19 | p-$NO_2$—$C_6H_4$— | $C_6D_6$ | 6,60 | |
| 20 | p-$CH_3$—O—$C_6H_4$ | $CDCl_3$ | 6,95 | $CH_3$ at 3,86 |
| 21 | $C_6H_5$—CH=CH— | $CDCl_3$ | 6,73 | one of the 2-ethylenic protons visible at 7,03, J = 16,5 c/s |
| 22 | 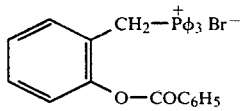 | $CDCl_3$ | 6,87 | $CH_3$ at 3,9 and 4,0 |

The following example is designed to illustrate the preparation of the compounds according to the invention by a mechanism of the phase transfer type.

EXAMPLE 23

Preparation of 2-phenyl benzofuran

A solution of 0.02 mole of phosphonium salt of formula:

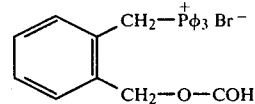

(prepared by the process of Example 4 or of Example 18) in 10 cc of $CH_2Cl_2$ is agitated for 1 hour in the presence of 10 cc of 40% caustic soda.

After evaporation of the organic phase, the residue is treated with 40 cc of toluene in order to eliminate the residual phosphonium salt. After filtration and evaporation of the toluene, the residue is treated with 30 cc of pentane. The pentane is then evaporated in order to isolate the 2-phenyl benzofuran with a yield in the order of 25%.

EXAMPLE 24

Preparation of isochrom-3-ene

A solution of 1 mole of triphenylphosphine and 1 mole of α,α'-dibromoxylene is heated under reflux for 2 hours in toluene. A phosphonium salt having the following formula is obtained:

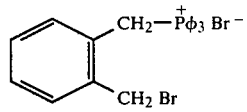

with a yield of 98%.

This phosphonium salt, after several hours under reflux in a hydroacetonic solution of sodium formate, leads to the formation of the derivative of formula:

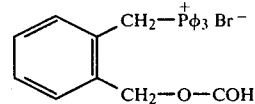

with a practically quantitative yield.

This compound, treated with a sodium t-amylate solution as in Example 1, leads to the formation of isochrom-3-ene. This compound is isolated as in Example 1, by filtration of the sodium bromide and evaporation of the toluene, followed by separation of the triphenylphosphine by a treatment with pentane.

This compound presents the features which are set out in Table III.

EXAMPLES 25 and 26

By replacing the sodium formate used in Example 24 by sodium acetate, the 2-methyl isochrom-3-ene is obtained, which shows the characteristics which are given in Table III, and by using sodium benzoate, the 2-phenyl isochrom-3-ene is obtained, which presents the features as given in Table III.

TABLE III

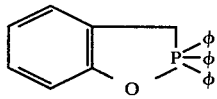

| Example No. | R | Yield (%) (a) | (b) | E (°C./mm Hg) | NMR spectrum (c) CH$_2$ | H | R |
|---|---|---|---|---|---|---|---|
| 24 | H | 47 | 42 | 83–84/8 | 5.11 | 5.86(d) | 6.64(d) |
| 25 | —CH$_3$ | 15 | 13 | 57–58/1 | 5.09 | 5.65 | 1.95 |
| 26 | —φ | 22.5 | 19 | F(alc) = 120–121 Lit: 124–125 | 5.28 | 6.55 | — |

(a) starting with phosphonium salts, as pure product (after distillation or recrystallisation)
(b) starting with α-α'-dibromoxylene
(c) δ, in relation to TMS in CDCl$_3$
(d) J = 6 c/s

EXAMPLE 27

Preparation of chrom-3-ene 1 mole of the phosphonium salt obtained according to stage (D) of Example 11 is treated with an equimolar quantity of sodium t-amylate in dichloromethane and as a result there is obtained the oxaphospholene of formula:

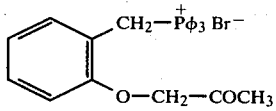

which is not isolated. An equimolar quantity of bromomethyl methyl ketone is caused to react with the reaction mixture, and after 30 minutes under reflux, the salt having the following formula is obtained:

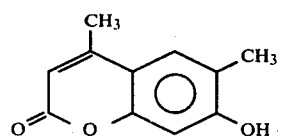

with a yield of about 75%.

The cyclisation is effected by dropwise addition of a solution of sodium t-amylate in toluene to the aforementioned phosphonium salt in suspension in the same solvent heated under reflux. After each addition, the yellow colouring of the phosphorane appears and then disappears almost immediately. After filtration of the sodium bromide, the toluene is evaporated and the 3-methyl chrom-3-ene is separated from the triphenyl phosphine oxide by a treatment with pentane.

Thus, a product is obtained which shows the characteristics which are given in Table IV.

EXAMPLES 28 and 29

Operating as indicated in Example 27, but replacing the bromomethyl methyl ketone by benzyl bromomethyl ketone, the 3-phenyl chrom-3-ene is obtained, which shows the characteristics which are given in Table IV, and with the use of p-nitrophenyl bromomethyl ketone, the 3-(p-nitrophenyl)-chrom-3-ene is obtained, which has the characteristics given in Table IV.

TABLE IV

| Example No. | R' | Yield (%) (a) | E (°C./mm) | NMR spectrum (b) CH$_2$ | H | R' |
|---|---|---|---|---|---|---|
| 27 | —CH$_3$ | 48 | 100–101/3.5 (d) | 4.71 | 6.23 | 1.80 |
| 28 | —φ | 65 | M.p.(alc.) = 87 | 5.23 (e) | (c) | — |
| 29 | ⟨phenyl⟩—NO$_2$ | 80 | M.p.(alc.) = 142 | 5.24 (e) | (c) | — |

(a) relative to the pure phosphonium salt
(b) in CDCl$_3$, ref. TMS
(c) signal protected by the aromatic mass
(d) Lit. B.p.$_2$ = 64°–65° C.
(d) J = 1.5 c/s.

EXAMPLE 30

Preparation of 2,5-dimethyl psoralene

A Pechmann condensation is carried out by the action of an equimolar quantity of 2,4-dihydroxy toluene on ethyl acetyl acetate in the presence of a Friedel-Crafts catalyst (AlCl$_3$). The compound having the following formula is obtained:

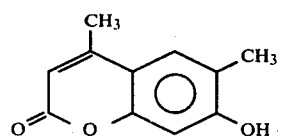

By operating as indicated in Example 1, but using the foregoing compound in place of o-cresol and acetyl chloride in place of propionyl chloride, there is obtained the phosphonium salt of formula:

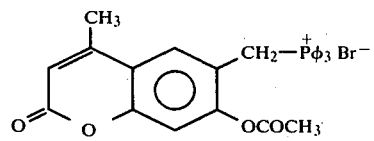

with a yield of 70%

NMR (CDCl$_3$): CH$_2$, 5.65 ppm (J$_{P-H}$=15 c/s), H (coumarine) at 6.25 ppm.

By cyclisation, as in Example 1, there is obtained the 2,5-dimethyl psoralene of formula:

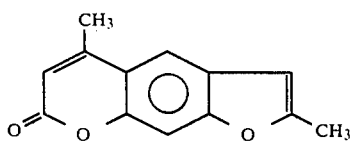

with a yield of 70%.

NMR (CDCl₃), furan and pyrone methyls, merged and centred at 2.48 ppm, ethylenic H at 6.35 and 6.58 ppm.

EXAMPLE 31

Preparation of 4,7-dimethyl furo-[2,3-h]-coumarine

Operating as in Example 30, but starting with 2,6-dihydroxy toluene, there is obtained the compound of formula:

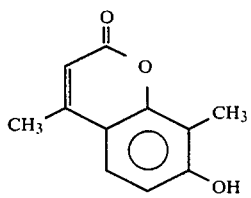

with a yield of 85%, then the phosphonium salt of formula:

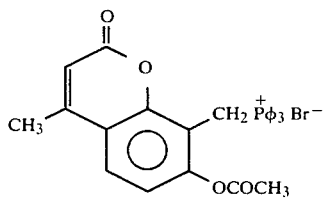

with a yield of 60%.

NMR (CDCl₃): methyl at 2.33 and 2.41 ppm $CH_2-P$ 5.38 ppm ($J_{P-H}$=14 c/s), pyronic H 6.08 ppm.

This cyclised compound leads to the 4,7-dimethyl furo[2,3-h]-coumarine of formula:

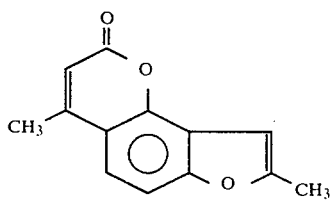

with a yield of 65%.

EXAMPLE 32

Preparation of 7-methyl-2-phenyl furo-[2,3-h]-coumarine

Operating as in Example 31, using benzoyl chloride instead of acetyl chloride, there is obtained the compound of formula:

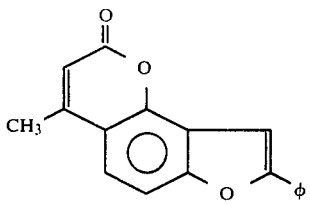

NMR (CDCl₃) pyronic methyl at 2.46 ppm pyronic H: 6.33 ppm and furanic H at 7.40 ppm.

Example 30 gives access to the derivatives of psoralene and Examples 31 and 32 to the derivatives of angelicine.

EXAMPLE 33

The 1-pentanoyloxy-2-bromomethyl benzene is prepared in the manner which is described in Example 2.

Then a solution of 0.1 M (37 g) of TOP in 30 cc of toluene has added thereto 0.1 M (27.1 g) of brominated ester. After 30 minutes at 100°–110° C., the quaternisation is complete.

The *liquid* mixture as obtained then has added thereto dropwise 0.1 M of sodium t-amylate (about 30 cc of a 3 to 3.5 N toluene solution) for 15 to 10 minutes; the cyclisation reaction is instantaneous.

The mixture obtained, formed of: t-AmOH, toluene, 2-butyl benzofuran, trioctylphosphine oxide (TOPO) and NaBr, is distilled under atmospheric pressure (thereby obtaining a t-AmOH-toluene mixture and then pure toluene), and then under reduced pressure (about 1 mm.Hg). At this stage, the 2-butyl benzofuran is recovered (with a purity higher than 95%) with a yield of about 85%.

The TOPO+NaBr residue is treated with 200 cc of water and then filtered at normal temperature. Yield of TOPO: 108% (this yield, higher than the theoretical yield, is due to the fact that the TOPO presents a purity from 92 to 93%).

We claim:

1. Process for the preparation of oxygenated heterocyclic compounds of Formula I:

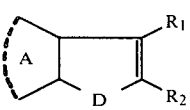

in which

represents a cycle of aromatic character, when D represents the radical —O—, $R_1$ and represents a hydrogen atom or a lower alkyl, aryl, aralkyl or cycloalkyl radical and, when D represents

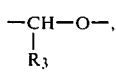

$R_1$ and $R_3$ represent a hydrogen atom, or a lower alkyl, aryl, aralkyl, alkenyl, alkynyl, aralkenyl, aralkynyl, cycloaliphatic radical, $R_{10}$—O—,

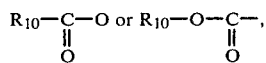

wherein $R_{10}$ is alkyl, alkenyl, alkynyl, aryl, aralkyl, aralkenyl, aralkynyl or cycloaliphatic radical and $R_2$ represents H or an organic radical, characterized in that a compound of Formula II:

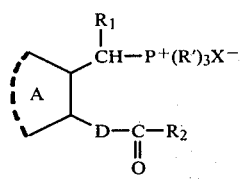

in which R' represents an alkyl, aryl or aralkyl radical and $X^-$ is an anion, is cyclized in the presence of a base in liquid phase.

2. Process according to claim 1, characterised by using a base capable of deprotonising the carbon in α-position of the phosphonium grouping.

3. Process according to claim 2, characterised in that the base is selected from the hydroxides and the alcoholates of alkali metals.

4. Process according to claim 3, characterised in that the base is selected from sodium t-amylate and potassium t-butylate.

5. Process according to claim 3, characterised in that the base is selected from caustic soda and caustic potash.

6. Process according to claim 1, characterised in that the liquid medium being used is a non-polar aprotic solvent or a mixture of non-polar aprotic solvents.

7. Process according to claim 6, characterised in that the non-polar aprotic solvent is selected from the aromatic hydrocarbons, the halogenated aliphatic hydrocarbons and the ethers.

8. Process according to claim 7, characterised in that the non-polar aprotic solvent is selected from toluene, dichloromethane and chloroform.

9. Process according to claim 1, characterised in that the liquid medium contains water.

10. Process according to claim 1, characterised in that the cyclisation is conducted under reflux of the reaction medium and at ambient pressure.

11. Process according to claim 1, characterised in that the compound of formula IIa:

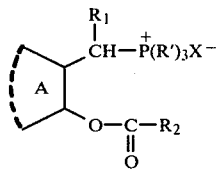

is prepared by action of phosphine $P(R')_3$ on a compound of formula IIIa)

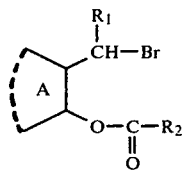

12. Process according to claim 1, characterised in that the compound of formula IIa:

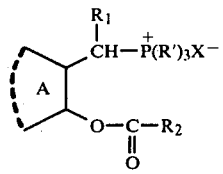

is prepared by esterification of the compound IIIac:

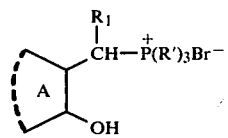

with an acid chloride of the following formula, or the corresponding anhydride:

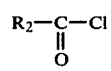

13. Process according to claim 1, characterised in that the compound of formula IIc:

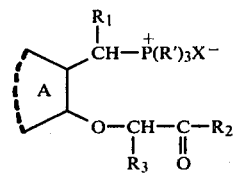

is obtained by etherification of the oxaphospholene of formula:

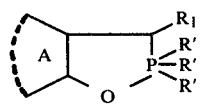

with a ketone of formula

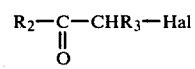

in a solvent.

14. Process according to claim 13, characterised in that the oxaphospholene is prepared by action of a base in a solvent on the compound of formula IIIac:

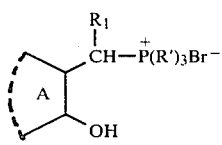 (IIIac)

15. Process according to claim 12, characterised in that the compound of formula IIIac is obtained from a compound of formula:

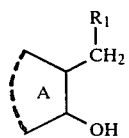

by esterification with the aid of acetyl chloride for forming the compound of formula VIac:

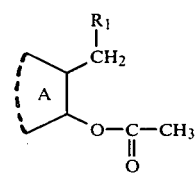 (VIac)

bromination of the compound as obtained for forming the compound of formula Vac:

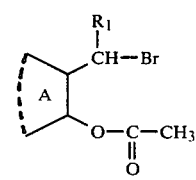 (Vac)

action of phosphine of formula P(R')₃ on this compound for forming the compound of formula IVac

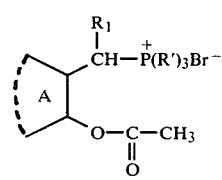 (IVac)

and hydrolysis of the preceding compound.

16. Process according to claim 11, characterised in that the compound of formula IIIa is prepared by bromination of the compound of formula IVa:

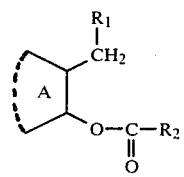 (IVa)

obtained by esterification of the compound of formula:

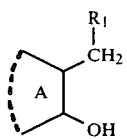

with the acid chloride

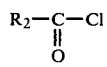

or the corresponding anhydride.

17. Process according to claim 1, characterised in that the compound of formula IIb:

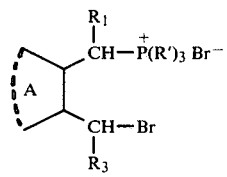 (IIb)

is obtained from the compound of formula:

$$R_2\text{—}C\text{—}Cl$$ (in image)

by treatment with the aid of a phosphine of formula P(R')₃ in toluene for forming the compound of formula IIIb:

(IIIb)

which, by treatment with the aid of a carboxylate of formula

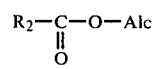

in which Alc represents an alkali metal, gives the compound IIb.

18. Process according to claim 1, characterised in that

represents a benzene ring which is substituted one or more times by an organic radical.

19. Process according to claim 1, characterised in that the compound which is prepared is 2-ethyl benzofuran, 2-butyl benzofuran, 2-i-propyl benzofuran or 4-aryloxy benzofuran.

20. Process according to claim 1, characterised in that R' is the phenyl radical or the octyl radical.

21. Process according to claim 20, characterised in that R' represents the octyl radical and in that the trioctyl phosphine oxide (TOPO) is separated from the reaction mixture.

* * * * *